(12) United States Patent
Konesky et al.

(10) Patent No.: US 9,649,143 B2
(45) Date of Patent: May 16, 2017

(54) ELECTROSURGICAL SYSTEM TO GENERATE A PULSED PLASMA STREAM AND METHOD THEREOF

(75) Inventors: Gregory A. Konesky, Hampton Bays, NY (US); Borislav S. Simeonov, St. Petersburg, FL (US)

(73) Assignee: BOVIE MEDICAL CORPORATION, Clearwater, FL (US)

( * ) Notice: Subject to any disclaimer, the term of this patent is extended or adjusted under 35 U.S.C. 154(b) by 1335 days.

(21) Appl. No.: 12/887,684

(22) Filed: Sep. 22, 2010

(65) Prior Publication Data

US 2011/0071517 A1 Mar. 24, 2011

Related U.S. Application Data

(60) Provisional application No. 61/244,911, filed on Sep. 23, 2009.

(51) Int. Cl.
*A61B 18/00* (2006.01)
*A61B 18/04* (2006.01)

(52) U.S. Cl.
CPC ................ *A61B 18/042* (2013.01)

(58) Field of Classification Search
CPC .......................... A61B 2018/00583
USPC ...................... 606/32, 41
See application file for complete search history.

(56) References Cited

U.S. PATENT DOCUMENTS

| | | | |
|---|---|---|---|
| 1,889,609 A | 11/1932 | Mutscheller | |
| 2,835,254 A | 5/1958 | Coles | |
| 3,299,384 A | 1/1967 | Lee | |
| 3,434,476 A * | 3/1969 | Shaw et al. | 606/22 |
| 3,577,030 A | 5/1971 | Cusick et al. | |
| 3,601,126 A | 8/1971 | Estes | |
| 3,692,973 A * | 9/1972 | Oku et al. | 219/121.46 |
| 3,877,843 A * | 4/1975 | Fischel | 417/394 |
| 3,949,266 A | 4/1976 | Vogts et al. | |
| 3,970,088 A | 7/1976 | Morrison | |
| 3,987,795 A | 10/1976 | Morrison | |
| 4,040,426 A | 8/1977 | Morrison, Jr. | |
| 4,041,952 A | 8/1977 | Morrison, Jr. et al. | |
| 4,043,342 A | 8/1977 | Morrison, Jr. | |

(Continued)

OTHER PUBLICATIONS

Panayiotis Diplas et al., "The Role of Impulse on the Initiation of Particle Movement Under Turbulent Flow Conditions"; Science, Oct. 31, 2008, vol. 322, pp. 717-720.

*Primary Examiner* — Ronald Hupczey, Jr.
(74) *Attorney, Agent, or Firm* — Gerald E. Hespos; Michael J. Porco; Matthew T. Hespos

(57) ABSTRACT

An electrosurgical system to generate a pulsed plasma stream and method thereof are provided. The system includes an electrosurgical generator coupled to an electrical power source to supply power for the electrosurgical system; a plasma generator including a noble gas conduit and an electrode disposed with the noble gas conduit, the electrode operatively coupled to the electrosurgical generator to selectively receive electrical energy therefrom such that the electrode at least partially ionizes a carrier gas feed to the noble gas conduit to create a plasma discharge; and a flow controller coupled to the noble gas conduit to pulse the flow of the carrier gas from a gas source to the noble gas conduit such that when the electrode is energized pulses of plasma discharge are generated at the surgical site.

24 Claims, 7 Drawing Sheets

(56) References Cited

U.S. PATENT DOCUMENTS

| | | |
|---|---|---|
| 4,060,088 A | 11/1977 | Morrison et al. |
| 4,255,735 A | 3/1981 | Liautaud |
| 4,429,694 A | 2/1984 | McGreevy |
| 4,492,231 A | 1/1985 | Auth |
| 4,547,721 A | 10/1985 | Drapp |
| 4,559,943 A | 12/1985 | Bowers |
| 4,781,175 A * | 11/1988 | McGreevy et al. ............ 606/40 |
| 4,818,916 A | 4/1989 | Morrisroe |
| 4,887,005 A | 12/1989 | Rough et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,999,597 A | 3/1991 | Gaynor |
| 5,088,997 A | 2/1992 | Delahuerga et al. |
| 5,302,881 A | 4/1994 | O'Loughlin |
| 5,325,019 A | 6/1994 | Miller et al. |
| 5,669,904 A | 9/1997 | Platt, Jr. et al. |
| 5,710,486 A | 1/1998 | Ye et al. |
| 5,717,293 A | 2/1998 | Sellers |
| 5,720,745 A | 2/1998 | Farin et al. |
| 5,776,092 A | 7/1998 | Farin et al. |
| 5,801,489 A | 9/1998 | Chism, Jr. et al. |
| 5,815,047 A | 9/1998 | Sorensen et al. |
| 5,917,286 A | 6/1999 | Scholl et al. |
| 6,046,546 A | 4/2000 | Porter et al. |
| 6,135,998 A | 10/2000 | Palanker |
| 6,154,376 A | 11/2000 | Dan-Harry |
| 6,181,068 B1 | 1/2001 | Hur et al. |
| 6,213,999 B1 | 4/2001 | Platt, Jr. et al. |
| 6,222,321 B1 | 4/2001 | Scholl et al. |
| 6,262,538 B1 | 7/2001 | Keller |
| 6,328,760 B1 | 12/2001 | James |
| 6,387,088 B1 | 5/2002 | Shattuck et al. |
| 6,529,389 B2 | 3/2003 | Perlick et al. |
| 6,629,974 B2 * | 10/2003 | Penny .................. A61B 18/042 128/898 |
| 6,807,069 B2 | 10/2004 | Nieminen et al. |
| 6,852,112 B2 | 2/2005 | Platt |
| 6,890,332 B2 | 5/2005 | Truckai et al. |
| 7,316,682 B2 | 1/2008 | Konesky |
| 8,057,468 B2 | 11/2011 | Konesky |
| 8,353,905 B2 | 1/2013 | Jensen et al. |
| 8,377,388 B2 * | 2/2013 | Konesky ....................... 422/292 |
| 8,388,615 B2 | 3/2013 | Bystryak et al. |
| 8,409,190 B2 | 4/2013 | Konesky et al. |
| 2001/0034519 A1 | 10/2001 | Goble et al. |
| 2002/0161362 A1 | 10/2002 | Penney et al. |
| 2004/0116918 A1 | 6/2004 | Konesky |
| 2005/0234442 A1 | 10/2005 | Spears |
| 2008/0108985 A1 | 5/2008 | Konesky |
| 2009/0024122 A1 * | 1/2009 | Fischer ........................... 606/40 |
| 2011/0139751 A1 * | 6/2011 | Koo et al. ....................... 216/67 |
| 2011/0184408 A1 | 7/2011 | Konesky et al. |

* cited by examiner

ELECTROSURGICAL SYSTEM TO GENERATE A PULSED PLASMA STREAM AND METHOD THEREOF

PRIORITY

This application claims priority to U.S. Provisional Patent Application No. 61/244,911 filed on Sep. 23, 2009, the contents of which are hereby incorporated by reference in its entirety.

BACKGROUND

Field

The present disclosure relates generally to electrosurgery and electrosurgical systems and apparatuses, and more particularly, to an electrosurgical system to generate a pulsed plasma stream and method thereof.

Description of the Related Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

SUMMARY

The present disclosure relates to an electrosurgical system to generate a pulsed plasma stream to perform electrosurgery on a surgical site on a patient. The system and method of the present disclosure provides a pulsed plasma stream to a surgical site by modulating and/or pulsing the gas flow for a plasma jet. Due to the pressure build-up of the carrier gas between pulses, a substantial impulse of gas occurs upon each applied pulse. This impulse of gas will assist in electrosurgical applications such as tissue ablation, tumor removal, etc. by accelerating the removal of debris.

Furthermore, the rapid inrush of gas increases cooling in low power temperature-sensitive applications.

According to one aspect of the present disclosure, an electrosurgical system includes an electrosurgical generator coupled to an electrical power source to supply power for the electrosurgical system and a plasma generator including an electrode operatively coupled to the electrosurgical generator to selectively receive electrical energy therefrom and to generate the plasma stream. A noble gas conduit coupled to a noble gas source to feed noble gas such as helium or argon to the noble gas conduit surrounds the electrode to at least partially ionize the noble gas to create the plasma stream. A flow controller is further provided to modulate and/or pulse the flow of the carrier or noble gas from the gas source to the gas conduit such that when the electrode is energized pulses of plasma discharge are generated at the surgical site.

According to another aspect of the present disclosure, a method for treating tissue at a surgical site of a patient is provided, the method including applying a first pulse of plasma by an electrosurgical handpiece to targeted tissue at a surgical site, wherein the first plasma pulse causes first eschar to be formed on the targeted tissue; and applying at least one subsequent pulse of plasma by the electrosurgical handpiece to the targeted tissue, wherein the at least one subsequent plasma pulse dislodges the first eschar and forms second eschar on the targeted tissue.

In another aspect, the method further includes applying a gas by the electrosurgical handpiece to the surgical site in between the first pulse and the at least one subsequent pulse to dislodge the formed eschar. In a further aspect, the method also includes applying a vacuum by the electrosurgical handpiece to the surgical site in between the first pulse and the at least one subsequent pulse to remove the dislodged eschar.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
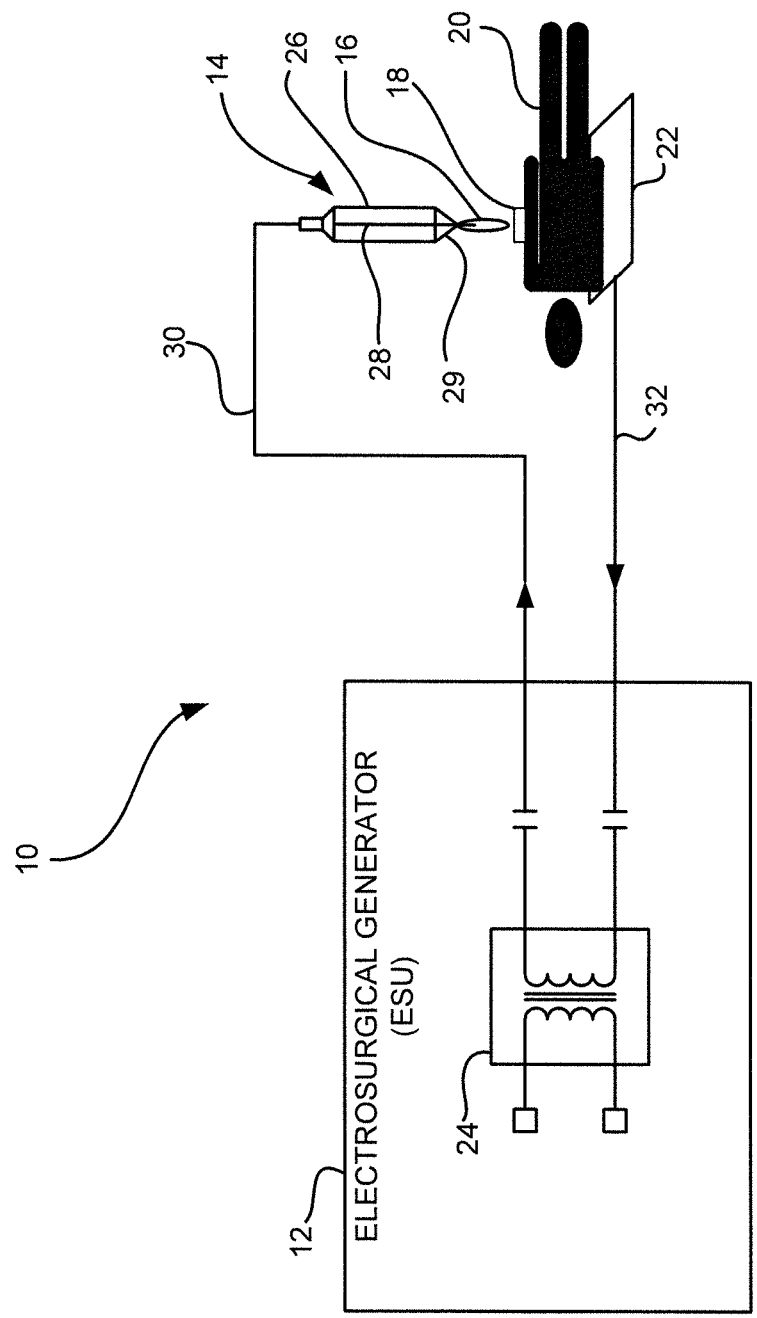
FIG. 1 is an illustration of a monopolar electrosurgical system in accordance with an embodiment of the present disclosure.

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

The present disclosure relates to an electrosurgical system to generate a pulsed plasma stream to perform electrosurgery on a surgical site on a patient. As described more fully hereinafter, the electrosurgical system includes an electrosurgical generator to supply power to the electrosurgical device and a plasma generator operatively coupled to the electrosurgical generator to receive electrical power therefrom and to generate a pulsed plasma stream for application to a surgical site or target area on a patient.

The system and method of the present disclosure provides a pulsed plasma stream to a surgical site by modulating and/or pulsing the gas flow for a plasma jet. Due to the pressure build-up of the carrier gas between pulses, a substantial impulse of gas occurs upon each applied pulse. This impulse of gas will assist in electrosurgical applications such as tissue ablation, tumor removal, etc. by accelerating the removal of debris, e.g., loosening particles of eschar formed at the surgical site and moving the particles of debris away from the surgical site. This concept of debris removal using impulses is akin to the erosional and sediment transport phenomena described in "The Role of Impulse on the Initiation of Particle Movement Under Turbulent Flow Conditions" P. Diplas, et al., Science, Vol. 322, 31 Oct. 2008, pp. 717-720, the contents of which are hereby incorporated by reference in its entirety. In the afore-mentioned article, Diplas et al. demonstrated that in addition to the magnitude of instantaneous turbulent forces applied on a sediment grain, the duration of these turbulent forces is also important in determining the sediment's grain's threshold of motion, and that their product, or impulse, is a parameter suitable for determining particle movement. Furthermore, Diplas et al. formulate threshold conditions for particle displacement based on force magnitude and duration variables of an impulse.

Generally, the system and method of the present disclosure provides a first pulse of a plasma stream to a surgical site resulting in eschar being formed at least on the surface of the surgical site. A subsequent pulse of the plasma stream results in an impulse of gas which dislodges the eschar formed during first or previously applied pulse. It is to be appreciated that during the subsequent pulse dislodged particles of eschar may be removed or may be removed during even further subsequent pulses. It is further to be appreciated that during subsequent pulses, in addition to the dislodgement and removal of eschar, new eschar is being formed in accordance with the procedure being performed, e.g., an ablation procedure. Additionally, the rapid inrush of gas during each pulse increases cooling in low power temperature-sensitive applications.

It is to be appreciated that by employing the method of the present disclosure, i.e., applying pulses of plasma, the plasma beam created will remain focused, e.g., pinpoint, and therefore, be more effective than in conventional methods. In the conventional method of applying a continuous beam of plasma, the eschar formed creates a barrier over the targeted tissue which tends to disperse the plasma beam, and thus making it less effective over time. By pulsing the plasma beam, each subsequent plasma pulse dislodges and removes the previously formed eschar. In this manner, the removal of eschar by each pulse prevents the eschar barrier from forming and allows the plasma beam to stay focused enabling a more effective treatment of the target tissue, e.g., a shorter treatment time.

FIG. 1 shows a monopolar electrosurgical system generally indicated as 10 comprising an electrosurgical generator (ESU) generally indicated as 12 to generate power for the electrosurgical system 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The handpiece or holder 26 enables the plasma generator to be hand-held and manipulated by an operator close to or within a patient. The high frequency electrical energy is fed from the secondary of the transformer 24 through an active conductor 30 to the electrode 28 (collectively, "active electrode") in the handpiece 26 to create the plasma stream 16 for application to the surgical site 18 on the patient 20.

The return path to the electrosurgical generator 12 is through the tissue and body fluid of the patient 20, the conductor plate or support member 22 and a return conductor 32 (collectively, "return electrode") to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. The capacitance is determined, among other things, by the physical size of the patient 20. Such an electrosurgical system and generator are described in commonly owned U.S. Pat. No. 7,316,682 to Konesky, the contents of which are hereby incorporated by reference in its entirety.

Figure 2A:
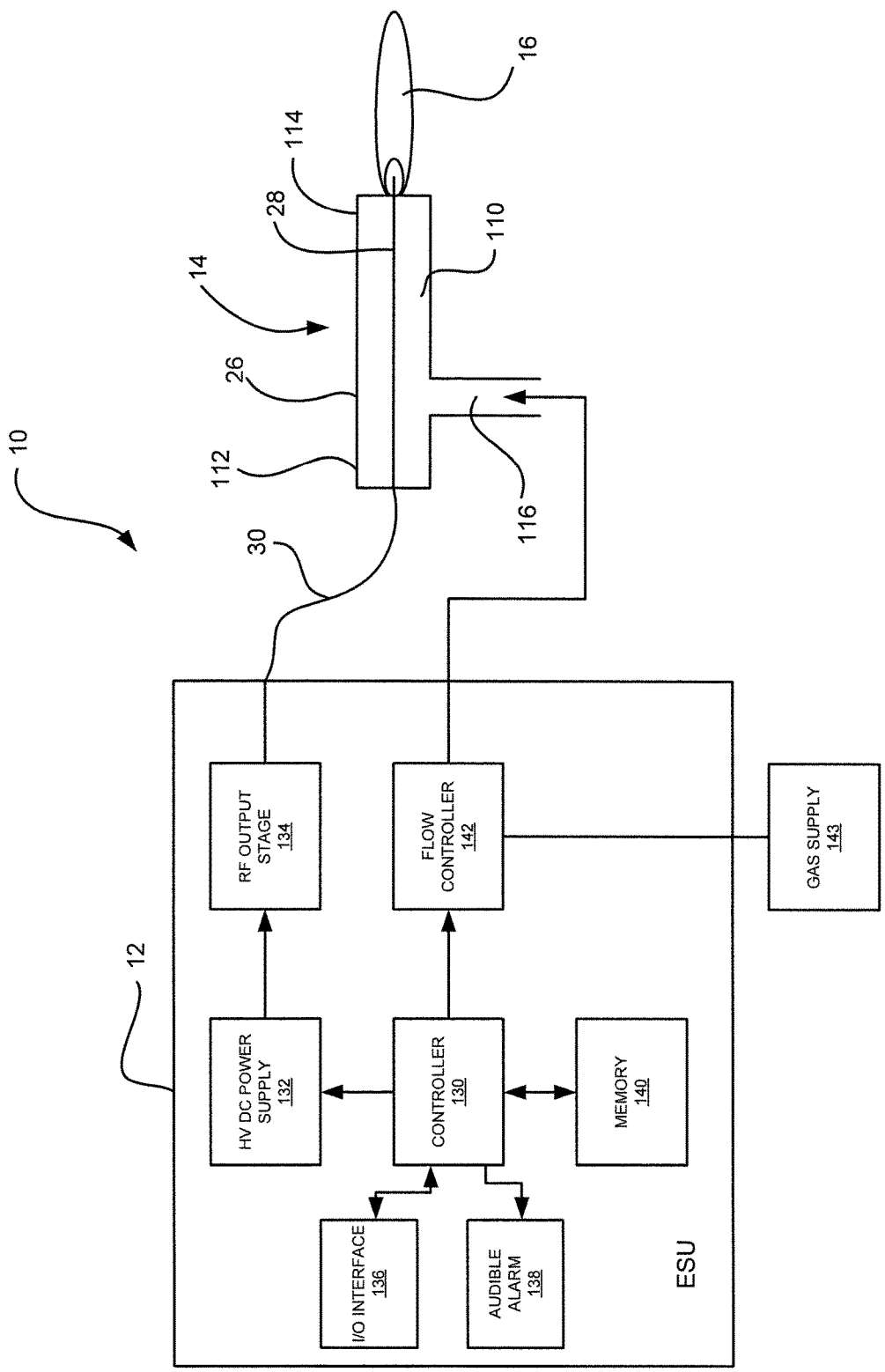
FIG. 2A is a block diagram of an electrosurgical generator and a plasma generator in accordance with an embodiment of the present disclosure.

Referring to FIG. 2A, the electrosurgical generator 12 and plasma generator 14 including the electrode 28 supported by the handpiece 26 and at least partially disposed in the fluid flow housing 29 is illustrated. The electrode 28 is concentrically disposed within an inner noble gas conduit 110 having a proximal end 112 and a distal end 114 coupled to a noble gas source 143 by a noble gas supply conduit 116 to feed noble gas such as helium or argon to the noble gas conduit 110. The conducting plasma stream 16 couples the electrosurgical generator 12 to the patient 20.

The electrosurgical generator 12 includes a controller 130 that controls a HV DC power supply 132 to supply electrosurgical energy being output from an RF output stage 134. The electrosurgical generator 12 will indicate various operating conditions to an operator via an I/O interface 136 such as a touch screen or an audible alarm 138.

The system 10 further includes a flow controller 142 for controlling the flow of gas to the plasma generator 14. The flow controller 142 modulates or pulses the flow of gas from the gas supply 143 to the plasma generator 14 creating pulses of plasma at the operative site. The flow controller 142 is coupled to the controller 130 and receives control signals from the controller 130 based on user input via I/O interface 136 or based on an algorithm or software function stored in memory 140.

Figure 2B:
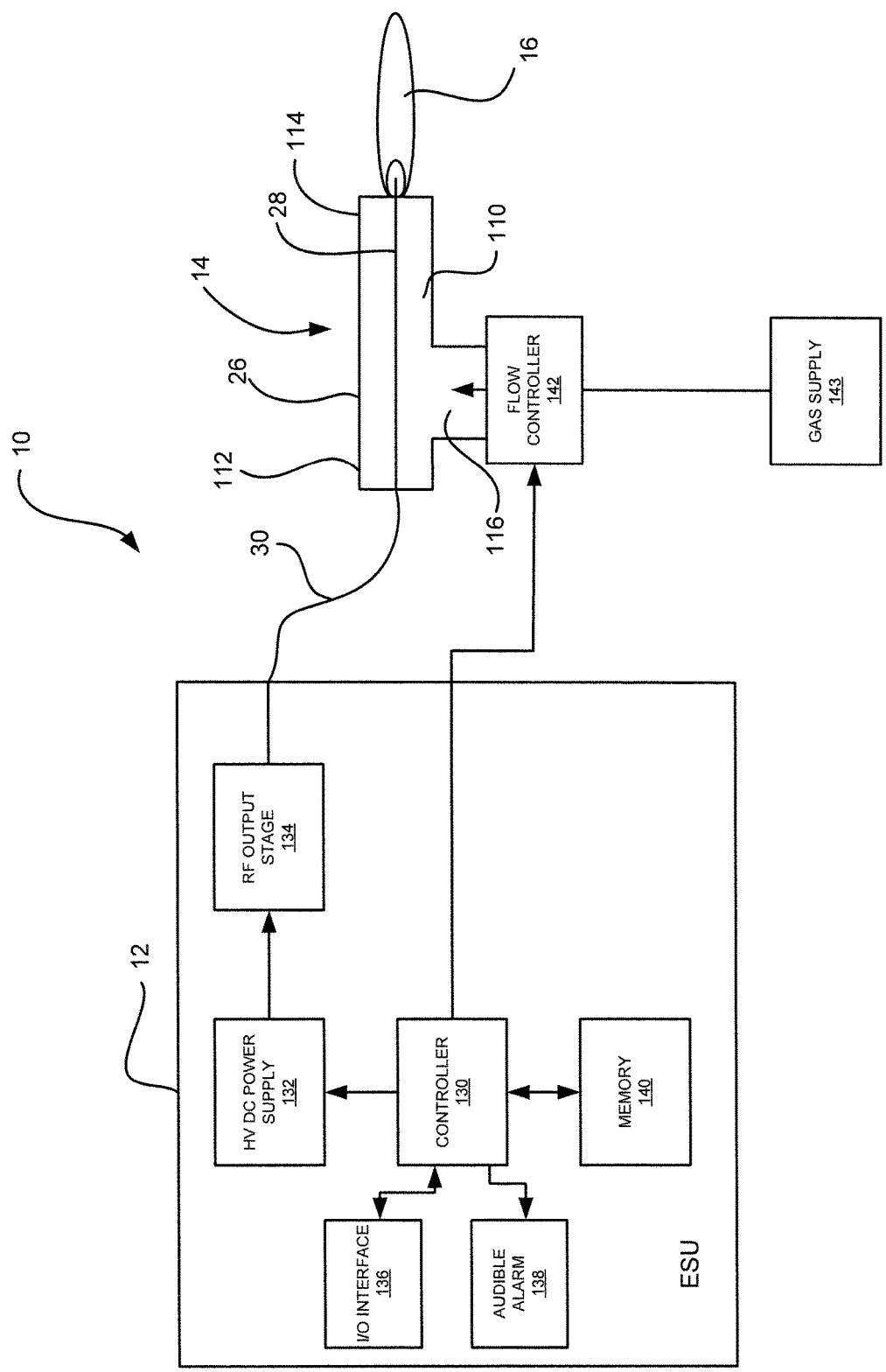
FIG. 2B is a block diagram of an electrosurgical generator and a plasma generator in accordance with another embodiment of the present disclosure.

Although in the embodiment shown, the flow controller 142 is disposed in the electrosurgical generator 12, the flow controller 142 can be located external to the electrosurgical generator 12 and disposed in a separate housing. It is to be appreciated that if an external flow controller 142 is employed, the external flow controller 142 will be controlled by controller 130 so that a single source will control the flow of gas and the supply of electrosurgical energy. Furthermore, in other embodiments, the flow controller 142 may be disposed in the plasma generator 14 itself, as shown in FIG. 2B.

Figure 3:
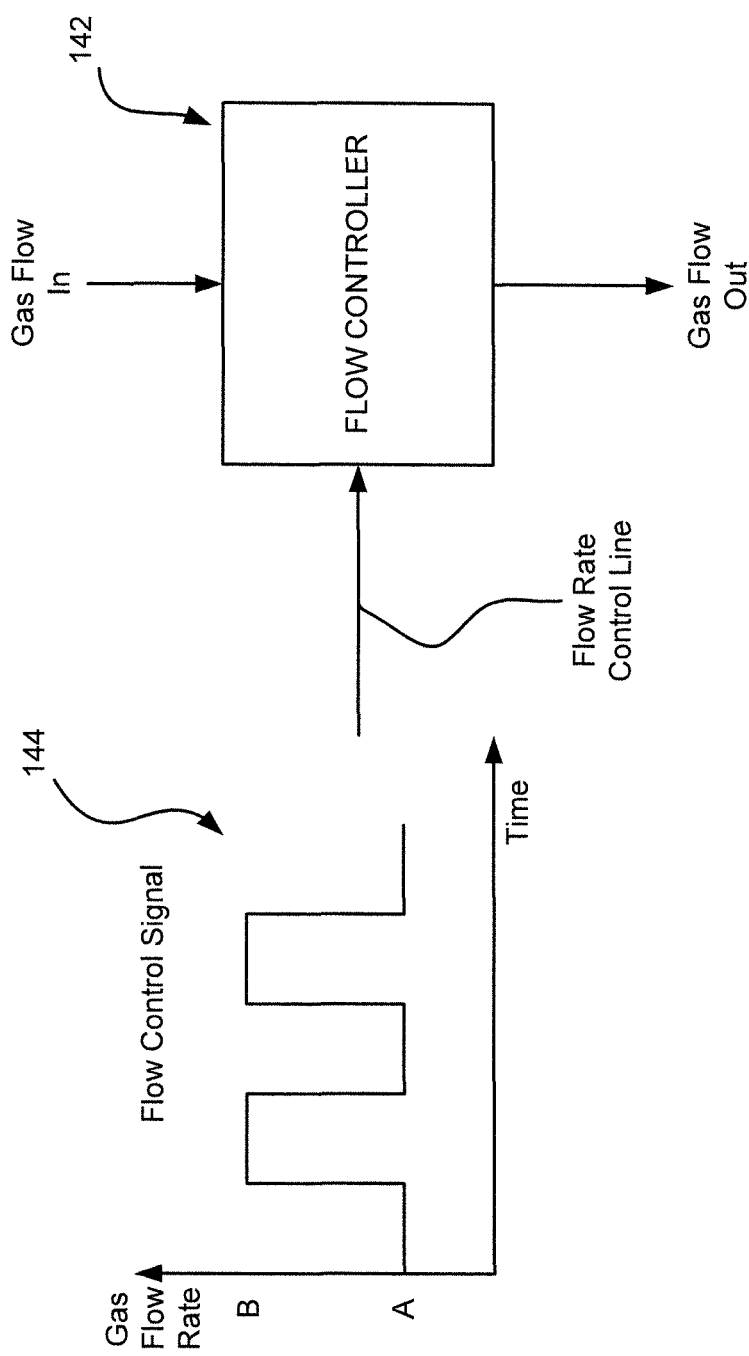
FIG. 3 is an illustration of a flow controller and associated flow control signal in accordance with an embodiment of the present disclosure.

Referring to FIG. 3, an embodiment of flow controller 142 is illustrated. In this embodiment, the flow controller 142 is a mass flow controller. Also shown is a controlling electrical signal waveform 144. The gas flow varies from a background level "A", which could be zero (i.e., flow off) to a maximum flow level "B" (i.e., full flow). A pulse waveform is illustrated but any arbitrary waveform may be employed. As the flow control signal is received from the controller 130, the flow controller 142 will modulate the gas flow from no flow to full flow, or a predetermined flow level, to create pulses of plasma at the plasma generator 14.

Figure 4:
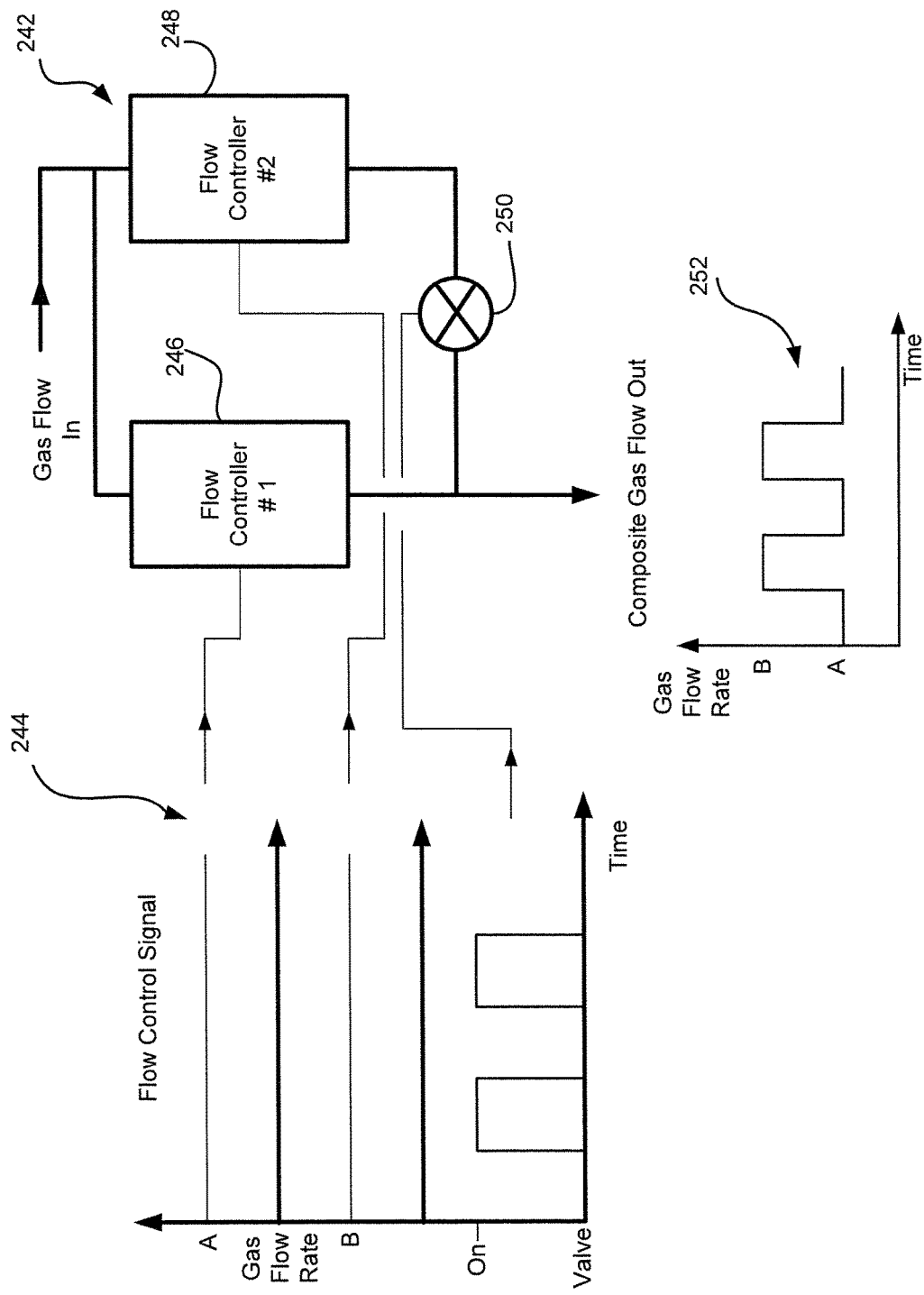
FIG. 4 is an illustration of dual flow controller and associated flow control signals in accordance with another embodiment of the present disclosure.

Some types of gas flow controllers, such as mass flow controllers, are not particularly fast in their ability to change flow rates and may require a few seconds to achieve a given set point. To counteract this, a dual control flow controller 242 is provided as shown in FIG. 4. The dual flow controller 242 includes a first flow controller 246, a second flow controller 248 and at least one valve 250.

The flow control signals 244 are illustrated for the first and second flow controller 246, 248 and the valve 250. The first flow controller 246 is set to a background level "A" and the second flow controller 248 is set to the maximum flow rate "B", each with continuous flow control signal levels. Valve 250, e.g., a solenoid valve, switches in the high flow rate from the second flow controller 248 in response to a flow control signal, e.g., a pulse or square wave signal. The resulting composite gas flow output graph 252 is also shown. It is to be appreciated that valve 250 may be switched up to several hundred times a second to achieve the desired effect.

Figure 5:
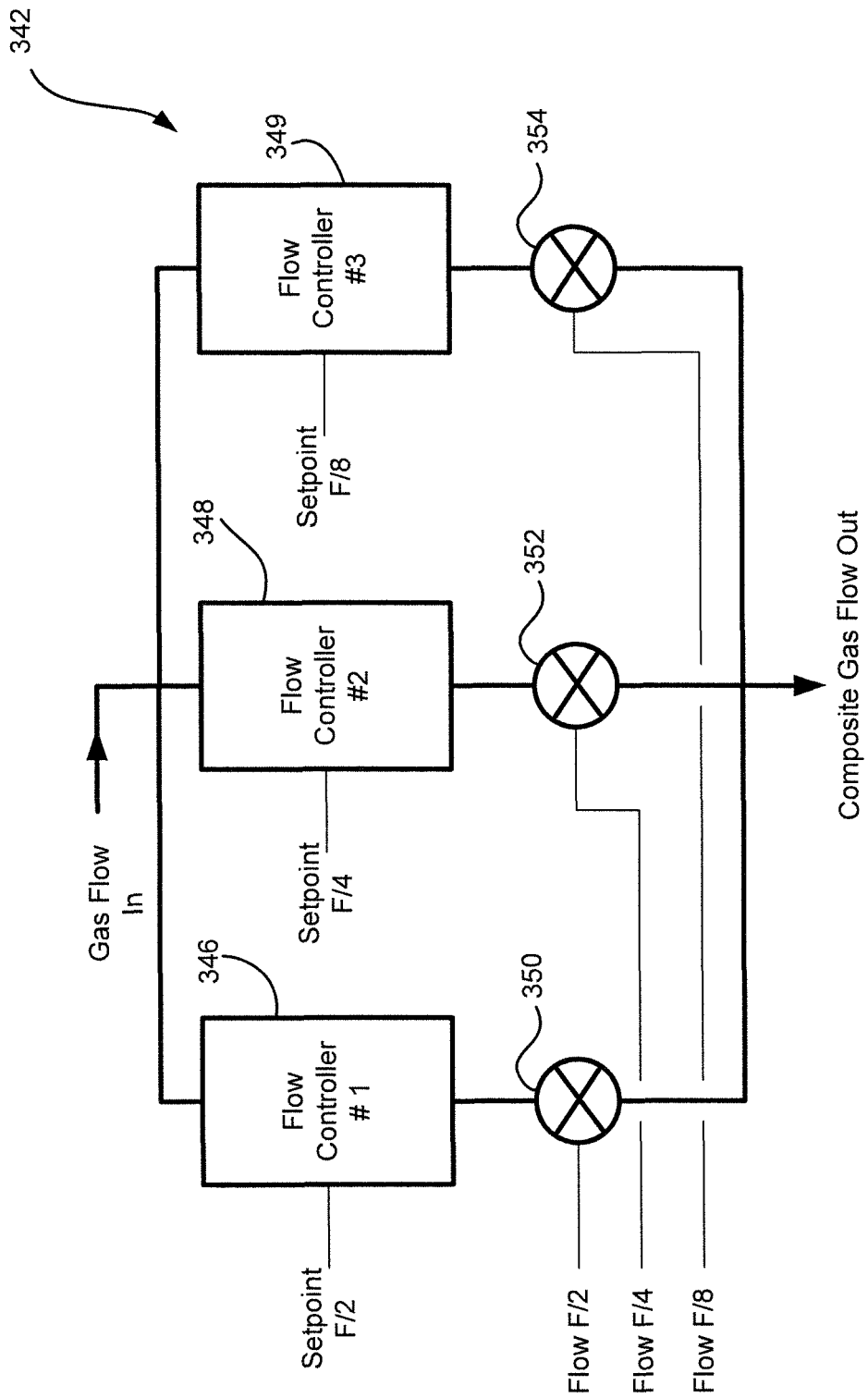
FIG. 5 is an illustration of a binary flow controller in accordance with an embodiment of the present disclosure.

Referring to FIG. 5, a binary flow controller 342 is provided. In this embodiment, multiple flow controllers 346, 348, 349 are employed, although only three are illustrated. The flow rate of each controller is set in a binary progression with the first flow controller 346 set at half the maximum flow rate, i.e., setpoint F/2, the second flow controller 348 set at one quarter of the maximum flow rate, i.e., setpoint F/4, the third flow controller 349 set at one eighth of the maximum flow rate, i.e., setpoint F/8, and so on. By switching in various combinations of solenoid valves, any arbitrary gas flow output can be achieved, even non-periodic (non-repeating) gas flow patterns. For example, if one eighth of the maximum flow rate is desired, then only the F/8 solenoid valve 354 would be activated. If the flow needs to be adjusted to three quarters of the maximum flow rate, then both the F/2 solenoid valve 350 and the F/4 solenoid valve 352 would be activated. All three valves on would produce 7/8 of the maximum flow rate.

The flow controllers described above provide a pulsed plasma stream to a surgical site by modulating and/or pulsing the gas flow for a plasma jet, which can be likened to a plasma hammer. Due to the pressure build-up of the carrier gas between pulses, a substantial impulse of gas occurs upon each applied pulse. This impulse of gas will assist in electrosurgical applications such as tissue ablation, tumor removal, etc. by accelerating the dislodgement and removal of debris. Furthermore, the rapid inrush of gas increases cooling in low power temperature-sensitive applications. Additional cooling of the site will occur between pulses.

In an exemplary embodiment of the electrosurgical system, the flow controllers will operate at a pulse repetition rate of approximately less than 1 Hertz (Hz) to approximately 500 Hz. The duty cycle of the pulses range from approximately less than 10% to more than 90%. The flow rate may range from approximately 1 Liter per Minute (LPM) to approximately 10 LPM. The power provided by the electrosurgical generator may be varied from approximately 15 Watts (W) to approximately 150 W. For most applications, the tip of the handpiece may be distanced from the target tissue approximately 1 mm to approximately 20 mm. It is to be appreciated that the above numbers and ranges are for illustrative purposes only and is in no way meant to limit the scope of the present disclosure.

It is to be appreciated that in the embodiments described above, the pulsed plasma effect is achieved by keeping the electrical signal to the electrode active at all times and only modulated and/or pulsing the gas flow. However, in other embodiments, the electrical signal applied to the electrode is modulated and/or pulsed along with the gas flow. For example, in one embodiment, both activating the electrical energy and gas flow is performed simultaneously. In other embodiments, the initiating of the process, i.e., the activating of the electrical energy and gas flow, may be performed on a particular phase of the electrical power waveform, such as a zero-crossing or at a peak voltage.

Figure 7:
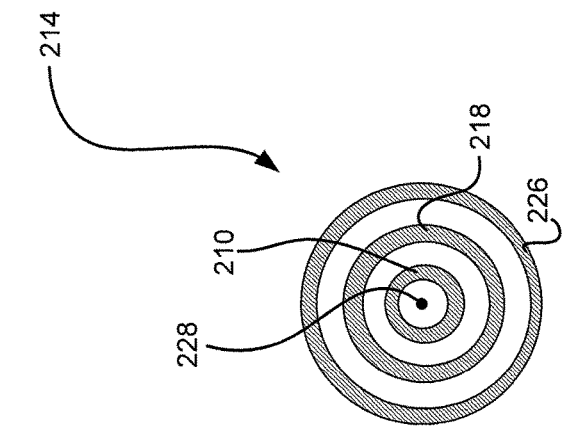
FIG. 7 is a cross sectional end view of the plasma generator of the electrosurgical system of the present taken along line 7-7 of FIG. 6.
Figure 6:
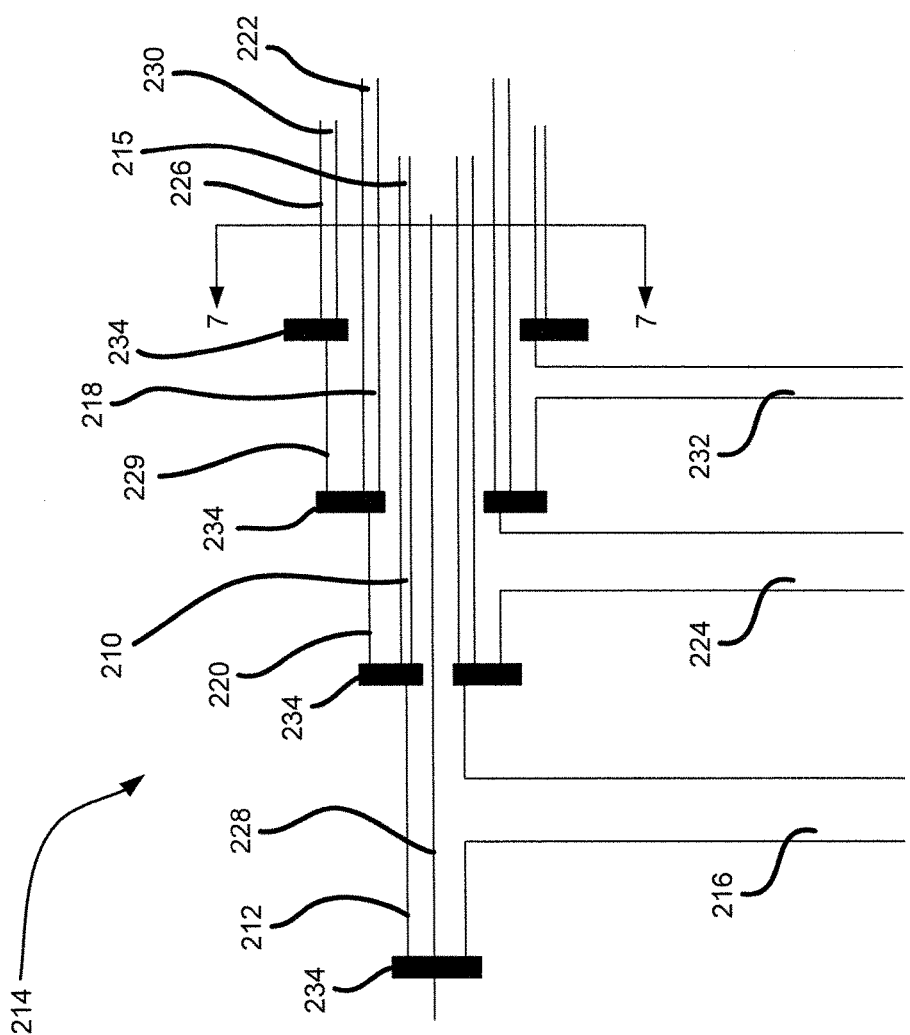
FIG. 6 is a partial diagrammatic side view of the plasma generator of the electrosurgical system of the present disclosure.

Referring to FIGS. 6 and 7, an embodiment of a plasma generator 214 to be employed in accordance with the teachings of the present disclosure is provided. The plasma generator 214 includes an electrode 228 supported by the handpiece 26 and at least partially disposed in the fluid flow housing 29. As previously described, the electrode 228 is operatively coupled to the electrosurgical generator 12 to selectively receive electrical energy therefrom. The electrode 228 is concentrically disposed within an inner noble gas conduit 210 having a proximal end 212 and a distal end 215 coupled to a noble gas source (not shown) by a noble gas supply conduit 216 to feed noble gas such as helium or argon to the inner noble gas conduit 210. An intermediate air or electronegative gas conduit 218 is disposed in surrounding coaxial relation relative to the noble gas conduit 210 having a proximal end 220 and a distal end 222 coupled to a gas source (not shown) by an air or electronegative gas supply conduit 224 to feed air or electronegative gas to the intermediate air or electronegative gas conduit 218. The distal end 215 of the inner noble gas conduit 210 is disposed inwardly from the distal end 222 of the intermediate electronegative gas conduit 218. Alternately, in place of the air or electronegative gas, noble gas may be fed through the intermediate air or electronegative gas conduit 218 to create a diffuse cylindrically shaped relatively wide area plasma beam useful with particular procedures such as dermatology.

An outer aspiration conduit 226 is disposed in surrounding coaxial relation relative to the intermediate air or electronegative gas conduit 218 having a proximal end 229 and a distal end 230 coupled to a negative pressure source such as a vacuum (not shown) by a negative pressure conduit 232 to remove fluid and solid debris from the target area 18 on the patient 20. The distal end 230 of the outer aspiration conduit 226 is disposed inwardly from the distal end 222 of the intermediate air or electronegative gas conduit 218. A plurality of seals each indicated as 234 are used to seal the noble gas conduit 210, the intermediate air or electronegative gas conduit 218 and the outer aspiration gas conduit 226.

In one embodiment, a pulsed flow controller in accordance with the present disclosure is coupled to the noble gas supply conduit 216 to provide pulses of noble gas. In this embodiment, between pulses of plasma, the air or electronegative gas supply conduit 224 and the negative pressure conduit 232 remain operational to clean the surgical site and remove dislodged debris. For example, after a first pulse of plasma, eschar is formed at the surgical site. A subsequent pulse of the plasma stream results in an impulse of gas which dislodges the eschar formed during the first or previously applied pulse. After the subsequent pulse and in between further subsequent pulses, the air or electronegative gas is applied via the intermediate air or electronegative gas conduit 218 to clean the surgical site, i.e., dislodge eschar, where the negative pressure of the negative pressure conduit 232 then removes the dislodged debris.

In a further embodiment, when noble gas is fed through the intermediate air or electronegative gas conduit 218 to create a diffuse cylindrically shaped relatively wide area plasma beam, flow controllers in accordance with the present disclosure will be coupled to both the noble gas supply conduit 216 and the electronegative gas supply conduit 224.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. An electrosurgical system comprising:
   a plasma generator including a noble gas conduit and an electrode disposed within the noble gas conduit, the electrode configured to at least partially ionize a carrier gas fed through the noble gas conduit to create a plasma discharge at a distal end of the noble gas conduit;
   an electrosurgical generator including a high voltage power supply and a controller, the high voltage power supply configured to supply power to the electrode to enable the plasma generator to create the plasma discharge;
   a first flow controller having a first flow entry passage and a first flow exit passage, the first flow entry passage connected directly to an exit passage of a unitary gas source for receiving carrier gas directly from the unitary gas source, the first flow exit passage connected to a composite flow passage;
   a second flow controller arranged in parallel with the first flow controller, the second flow controller having a second flow entry passage and a second flow exit passage, the second flow entry passage connected directly to the exit passage of the unitary gas source for receiving carrier gas directly from the unitary gas source; and
   a valve having a third flow entry passage and a third flow exit passage, the third flow entry passage connected directly to the second flow exit passage, the third flow exit passage connected to the composite flow passage;
   wherein the composite flow passage is configured to feed carrier gas from at least one of the first flow controller and second flow controller through the noble gas conduit of the plasma generator;
   wherein the controller of the electrosurgical generator is configured to provide control signals to the first flow controller, the second flow controller, and the valve to thereby automatically create multiple pulses of a flow of the carrier gas through the noble gas conduit without user intervention; and
   wherein, when the high voltage power supply supplies power to the electrode of the plasma generator to energize the electrode, the multiple pulses of the flow of the carrier gas creates multiple pulses of plasma discharge at the distal end of the noble gas conduit.

2. The electrosurgical system of claim 1, wherein, in response to receiving the control signals from the controller of the electrosurgical generator, the first flow controller is configured to provide carrier gas from the first flow exit passage at a first flow rate, the second flow controller is configured to provide carrier gas from the second flow exit passage at a second flow rate, and the valve is configured to open and close in a periodic manner to provide pulses of carrier gas from the third flow exit passage.

3. The electrosurgical system of claim 2, wherein the composite flow passage is configured to provide a modulating flow of carrier gas to the noble gas conduit such that, when the electrode is energized, the plasma generator creates pulses of plasma discharge.

4. The electrosurgical system of claim 2, wherein the second flow rate is greater than the first flow rate.

5. The electrosurgical system of claim 1, further comprising a second valve interposed between the first flow controller and the composite flow passage, and further comprising at least one additional flow controller and at least one additional valve interposed between a respective additional flow controller and the composite flow passage.

6. The electrosurgical system of claim 5, wherein the flow rates of the first flow controller, second flow controller, and at least one additional flow controller are fixed in a binary progression relative to each other, and wherein in response to control signals received from the controller the valves switch in the flow rate of the corresponding flow controllers to provide a desired flow rate through the composite flow passage and create the pulses in the flow of the carrier gas through the nobles gas conduit.

7. The electrosurgical system of claim 1, wherein the plasma generator further includes an intermediate electronegative gas conduit including a distal end and a proximal end disposed in surrounding relation relative to the noble gas conduit to cooperatively form an electronegative gas channel therebetween coupled to a gas source to feed electronegative gas to the intermediate electronegative gas channel, the distal end of the intermediate electronegative gas conduit extending beyond the distal end of the noble gas conduit such that the electronegative gas sustains the plasma discharge.

8. The electrosurgical system of claim 7, wherein the plasma generator further includes an outer aspiration conduit disposed in surrounding relation relative to the intermediate electronegative gas conduit to cooperatively form an aspiration channel therebetween coupled to a negative pressure source, wherein the negative pressure source is configured to remove fluid and solid debris from the surgical site.

9. The electrosurgical system of claim 1, wherein the high voltage power supply is configured to supply direct current (DC) voltage.

10. The electrosurgical system of claim 1, wherein the controller is configured to create pulses of plasma discharge at a rate of at least about one pulse per second.

11. An electrosurgical generator comprising:
an electrical power source configured to supply electrosurgical energy to an electrode of a plasma generator; and
a controller that is configured to provide a first control signal to a first flow controller and a second control signal to a second flow controller;
wherein the first flow controller and second flow controller are arranged in parallel with each other such that an entry passage of each of the first flow controller and second flow controller is directly connected to an exit passage of a gas source to receive carrier gas directly from the gas source;
wherein the plasma generator comprises a noble gas conduit arranged to receive a composite flow of the carrier gas from the gas source by way of the first flow controller and second flow controller;
wherein the controller is configured to automatically control the composite flow of the carrier gas via the first flow controller and the second flow controller to provide multiple pulses of a flow of the carrier gas through the noble gas conduit without user intervention; and
wherein when the electrical power source supplies electrosurgical energy to the electrode of the plasma generator, the multiple pulses of the flow of the carrier gas create multiple pulses of plasma discharge at an output of the plasma generator.

12. The electrosurgical generator of claim 11, wherein the controller is configured to provide a third control signal to a valve connected to an exit passage of the second flow controller.

13. The electrosurgical generator of claim 12, wherein the valve is a solenoid valve.

14. The electrosurgical generator of claim 12, wherein the third control signal from the controller is a square wave configured to open and close the valve such that an exit passage of the valve provides a flow of carrier gas modulating between a minimum flow rate and a maximum flow rate of the second flow controller.

15. The electrosurgical generator of claim 11, wherein the electrosurgical generator comprises the first flow controller and second flow controller, wherein the first flow controller includes a first flow exit passage connected to a composite flow passage, and wherein the second flow controller includes a second flow exit passage connected to the composite flow passage.

16. The electrosurgical generator of claim 11, wherein the first control signal causes the first flow controller to provide carrier gas at a first flow rate, wherein the second control signal causes the second flow controller to provide carrier gas at a second flow rate, and wherein the first flow rate differs from the second flow rate.

17. The electrosurgical generator of claim 16, wherein the controller is configured to control the composite flow through the noble gas conduit to pass the carrier gas at a composite flow rate modulating between a minimum flow rate equal to the first flow rate and a maximum flow rate equal to the sum of the first flow rate and second flow rate.

18. The electrosurgical generator of claim 11, wherein the controller is configured to automatically create pulses of plasma discharge at a rate of at least about one pulse per second without user intervention.

19. An electrosurgical system comprising:
a plasma generator including a noble gas conduit and an electrode disposed within the noble gas conduit, the electrode configured to at least partially ionize a carrier gas fed through the noble gas conduit to create a plasma discharge at a distal end of the noble gas conduit;
an electrosurgical generator including a high voltage power supply, the high voltage power supply configured to supply power to the electrode to enable the plasma generator to create the plasma discharge; and
a flow controller having a first flow entry passage and a first flow exit passage, the first flow entry passage coupled to an exit passage of a gas source for receiving carrier gas directly from the gas source, the first flow exit passage coupled to the noble gas conduit to supply the carrier gas thereto,
the flow controller configured to control a flow rate of the carrier gas to the noble gas conduit by switching between a first flow rate and a second flow rate, the second flow rate being greater than the first flow rate, wherein the flow controller is configured to automatically switch between the first flow rate and the second flow rate to create multiple pulses in the carrier gas at the distal end of the noble gas conduit without user intervention, wherein, when the high voltage power supply supplies power to the electrode of the plasma generator to energize the electrode, the multiple pulses of the flow of the carrier gas create multiple pulses of plasma discharge at the distal end of the noble gas conduit.

20. The electrosurgical system of claim 19, wherein an initial pulse of plasma discharge is configured to create eschar on a surface of tissue at a surgical site and subsequent pulses of plasma discharge are configured to dislodge the previously created eschar and create new eschar.

21. The electrosurgical system of claim 20, wherein the plasma generator further includes an intermediate electronegative gas conduit including a distal end and a proximal end disposed in surrounding relation relative to the noble gas conduit to cooperatively form an electronegative gas channel therebetween coupled to a second gas source to feed electronegative gas to the intermediate electronegative gas channel in between pulses of the carrier gas to clean the surface of the tissue of dislodged eschar.

22. The electrosurgical system of claim 21, wherein the plasma generator further includes an outer aspiration conduit disposed in surrounding relation relative to the intermediate electronegative gas conduit to cooperatively form an aspiration channel therebetween coupled to a negative pressure source, wherein the negative pressure source is configured to remove fluid and dislodged eschar from the surgical site.

23. The electrosurgical system of claim 19, wherein the high voltage power supply is configured to maintain the power supplied to the electrode of the plasma generator while the multiple pulses of the flow of the carrier gas create the pulses of plasma discharge.

24. The electrosurgical system of claim 19, wherein the high voltage power supply is configured to modulate the power supplied to the electrode while the multiple pulses in the carrier gas are created such that the modulated power supplied to the electrode and the multiple pulses of the flow of the carrier gas create multiple pulses of plasma discharge at the distal end of the noble gas conduit.

* * * * *